(12) United States Patent
Brod

(10) Patent No.: US 7,625,554 B2
(45) Date of Patent: Dec. 1, 2009

(54) TREATMENT OF ALZHEIMER'S DISEASE

(76) Inventor: Staley A. Brod, 7015 Brook Run La., Houston, TX (US) 77040

( * ) Notice: Subject to any disclaimer, the term of this patent is extended or adjusted under 35 U.S.C. 154(b) by 991 days.

(21) Appl. No.: 10/655,164

(22) Filed: Sep. 4, 2003

(65) Prior Publication Data

US 2004/0105842 A1 Jun. 3, 2004

Related U.S. Application Data

(60) Provisional application No. 60/408,327, filed on Sep. 5, 2002.

(51) Int. Cl.
*A61K 38/00* (2006.01)
*C07K 14/00* (2006.01)
*C12Q 1/46* (2006.01)

(52) U.S. Cl. .................. 424/85.4; 530/351; 435/20

(58) Field of Classification Search ................ None
See application file for complete search history.

(56) References Cited

OTHER PUBLICATIONS

Brod SA, Kermoan RH, Nelson LD, Marshall GD, Henninger EM, Khan M, Jin R, Wolinsky JS. Ingensted IFN-alpha has biological efects in humans with relapsing-remitting multiple sclerosis. Mult Scler. Feb. 1997; 3(1):1-7.*
Greene YM, Tariot PN, Wishart H, Cox C, Holt CJ, Schwid S, Noviasky J. A 12-week, open trial of donepezil hydrochloride in patients with multiple sclerosis and associated cognitive impairments. J Clin Pschopharmacol. Jun. 2000; 20(3):350-6.*
Kujala P, Portin R, Ruutiainen J. The Progress of cognitive decline in multiple sclerosis. Brain. 1997. 120:289-297.*
Hutchinson M, Fazzini E. Cholinesterase inhibition in Parkinson's disease. J Neurol Neurosurg Psychiatry. Sep. 1996; 61(3):324-5.*
Steinman L, et al. Multiple sclerosis: Deeper understanding of its pathogenesis reveals new targets for therapy. 2002, Ann. Rev. Neurosci. vol. 25, p. 491-505.*
Brod S.A. Unregulated inflammation shortens human functional longevity. Inflammation Research. 2000. vol. 49, pp. 561-570.*

* cited by examiner

*Primary Examiner*—Gary B Nickol
*Assistant Examiner*—Bruce D Hissong
(74) *Attorney, Agent, or Firm*—Benjamin Aaron Adler

(57) ABSTRACT

The present invention provides a method for treating cognitive decline in a patient by administering to the patient at least about 100 units per day of α-interferon.

5 Claims, No Drawings

TREATMENT OF ALZHEIMER'S DISEASE

CROSS-REFERENCE TO RELATED APPLICATION

This non-provisional patent application claims benefit of provisional patent application U.S. Ser. No. 60/408,327, filed Sep. 5, 2002, now abandoned.

BACKGROUND OF THE INVENTION

1. Field of the Invention

The present invention relates generally to the fields neurology and treatment of cognitive decline. More specifically, the present invention relates to treating cognitive decline by oral administration of interferon, particularly type I interferons.

2. Description of the Related Art

Type I interferons (IFN) given by mouth have dramatic ameliorative effects in inflammatory states such as experimental allergic encephalomyelitis (EAE) and diabetes in animal mouse models of human disease (Brod and Khan, 1996). In humans with multiple sclerosis it has been shown that ingested human recombinant alpha interferon (hrIFN-α) is a biological response modifier that decreased pro-inflammatory cytokine production. Effects of the administration of interferon in multiple sclerosis patients are discussed in Brod (1997) and Brod et al. (1997).

The prior art is deficient in methods and compositions for treating cognitive decline utilizing the oral administration of interferon, particularly type I interferons. The present invention fulfills this long-standing need and desire in the art.

SUMMARY OF THE INVENTION

In one embodiment of the present invention, there is provided a method for treating cognitive decline in a patient by administering to the patient at least about 100 units per day of α-interferon.

In another embodiment of the present invention, there is provided a method for inhibiting or reducing the production or presence of cytokines, particularly in patients exhibiting cognitive decline, by administering to the patient at least about 100 units per day of α-interferon. Preferably, the α-interferon is administered orally.

Other and further aspects, features, and advantages of the present invention will be apparent from the following description of the embodiments of the invention given for the purpose of disclosure.

DETAILED DESCRIPTION OF THE INVENTION

One aspect of the present invention is a method for treating cognitive decline in a patient by administering to the patient at least about 100 units per day of α-interferon. Preferably, the α-interferon is administered orally. Also preferably, the α-interferon is administered every day. The amount of α-interferon administered every day can be about 2,000 units or more, but is preferably about 3,000 units or more, and more preferably about 10,000 units or more, such as 20,000 units, 25,000 units, 30,000 units, 35,000 units or more. If administered daily, the amount of α-interferon administered is preferably about 100 units or more, and can be, for example, 2,000 units or more but is preferably about 5,000 units or more. For example, about 10,000 units, 15,000 units, 20,000 units or more can be administered daily. Exact amounts can be determined by one skilled in the art based on characteristics of the patient to be treated and the severity of conditions to be treated. Characteristics of the patient that can affect the exact dosage required include age, gender, weight, extent of symptoms, potential interactions with other medications being taken by the patient, other medical conditions present in the patient and the like.

Another aspect of the invention is a method for inhibiting or reducing the production or presence of cytokines, particularly in patients exhibiting cognitive decline, by administering to the patient at least about 100 units per day of α-interferon. Preferably, the α-interferon is administered orally. Also preferably, the α-interferon is administered every day. The amount of α-interferon administered every day can be about 10,000 units or more, such as 20,000 units, 25,000 units, 30,000 units, 35,000 units or more.

It has been discovered that the oral administration of interferon in lower dosages than typically administered parenterally inhibits inflammatory diseases such as experimental allergic encephalomyelitis (EAE) and insulin dependent diabetes mellitus (IDDM). The inventor further discovered that oral administration of such relatively low dosages of interferon is effective in treating cognitive decline and/or symptoms thereof, such as, for example, cognitive decline associated with Alzheimer's Disease (AD) and other inflammatory/degenerative neurological diseases including Parkinson's Disease and Huntington's Disease. In particular, it has been observed that oral administration of certain dosages of interferon reduces the rate of cognitive decline in patients having mild to moderate cognitive decline. Furthermore, it has been found that oral administration of certain dosages of interferon decreases pro-inflammatory cytokine secretion by peripheral blood mononuclear cells. Cytokines the secretion of which is affected include IL-1, IL-6, and TGF-beta.

As used in the present invention, the term "cognitive decline" refers to cognitive decline exhibited in a battery of cognitive tests, wherein untreated or placebo patients declined 8% from baseline over one year.

As used in the present invention, "treatment of cognitive improvement" refers to the prevention of deterioration of cognitive functioning from baseline for one year.

Preferably, the a-interferon is administered in combination with an anticholinesterase agent such as donepezil. "In combination", as used herein, does not require that the drugs be administered simultaneously. For example, the donepezil may be administered once or more daily, while the interferon may be administered every other day. However, simultaneous administration of interferon and donepezil is within the scope of the invention.

The compounds and methods of the present invention can be used to treat a wide variety of disorders, but are especially useful in the treatment of cognitive decline and symptoms associated therewith. The disorders and symptoms treated can have a variety of origins and in some cases the origin of a disorder may not be apparent. For example, cognitive decline can be endogenously occurring; or due to environmental agents such as infectious, occupational, toxic, traumatic, or other causes. In particular, the compounds and methods of the present invention are expected to be effective in treating cognitive decline associated with Alzheimer's disease.

The compounds can be administered orally; parenterally, i.e., by subcutaneous, intravenous, or intramuscular injection; intraperitoneally; or by application to the mucous membranes of the nose, throat, bronchial tree, or eyes, etc. Oral administration is preferred. They may be administered alone or with suitable pharmaceutical carriers, and can be in solid or liquid form. Exemplary suitable dosage forms include tablets, capsules, powders, solutions, suspensions, and emulsions.

The dosage of the active compound depends on the species of warm-blooded animal, the body weight, age, and mode of administration. Appropriate dosage results in improvement of the cognitive performance and, in particular, causes an arrest or a reduction in the mass of the fibrocellular scar tissue or a decrease of the products it secrets, such as the levels of alpha 1-antichymotrypsin (ACT) procollagen peptides in serum.

Dosage forms can be prepared by processes known to those skilled in the art including dissolving, mixing, granulating, and/or tablet-coating processes. For oral administration, the active compounds or their physiologically acceptable derivatives such as salts, esters, or amides, can be mixed with additives customary for this purpose, such as carriers, stabilizers, or inert diluents, and made into suitable forms for administration, such as tablets, coated tablets, hard or soft gelatin capsules, aqueous, alcoholic, or oily suspensions, or aqueous, alcoholic or oily solutions, including saline solutions. Suitable carriers and vehicles include tablet bases such as lactose, sucrose, or cornstarch in combination with binders such as, for example, acacia, cornstarch, gelatin, cornstarch, potato starch, oils from animal, vegetable or mineral sources, and alginic acid. Also if desired, lubricants can be used, such as stearic acid or magnesium stearate. Capsules can contain the active compounds in the form of microspheres, wet or dry granules, powders, other particulate forms and the like.

The present invention is also directed to a method of treating an individual having Alzheimer's Disease or at risk for Alzheimer's Disease, comprising the step of administering to the individual a pharmacologically effective dose of alpha interferon. In one aspect, the alpha interferon may be administered orally. When administered orally, it is highly preferably that the alpha interferon is swallowed immediately by the individual. In this method of the present invention, the method may further comprise the step of: administering concomitantly to the patient pharmacologically effective dose of an anti-cholinesterase agent. A representative example of an anti-cholinesterase agent is donepezil. Generally, the alpha interferon is administered from about 100 units per day to about 35,000 units per day and may be administered by a method selected from the group consisting of oral administration, subcutaneous injection, intravenous injection and intramuscular injection.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Experimental Subjects

Sixty three subjects with Alzheimer's Disease having MMSE scores within the range 10-24 are selected. Subjects may not have taken any investigational medications within six weeks of baseline. All medications including OTC preparations used by the subject during and within one month of entry into the study are recorded in the study books and source documents. Prescription or OTC sympathomimitic amine and antihistamines are excluded for 48 hours prior to clinic visit. A complete medical, surgical, and psychiatric history is taken along with physical examination including EKG and clinical lab determinations (hemogram, chemistry profile, thyroid profile, $B_{12}$ and folic acid, serology, urinalysis).

Criteria for Inclusion of Subjects.
 1). Males and females, age 50 or older;
 2). Possible or probable dementia of the Alzheimer Type defined by NINDS-ARDA criteria with dementia of at least one year duration;
 3). Folstein MMSE Score 10-24 inclusive; and
 4). Vision, hearing, speech, motor function and comprehension must be adequate for compliance with all testing procedures.

Criteria for Exclusion of Subjects.
 1). Absence of a reliable caregiver;
 2). Clinical or radiological evidence for other neurological disorders such as normal pressure hydrocephalus, multi-infarct dementia, idiopathic seizure disorder, CNS infectious disease;
 3). History of major psychiatric disorders, schizophrenia and unipolar or bipolar depression;
 4). Presence of any significant medical disorder which might cause or contribute to dementia such as $B_{12}$ or folic acid deficiency, untreated hypothyroidism, history of significant alcohol abuse (within the past 10 years);
 5). Patients with recent (<2 years) hematologic/oncologic disorders (other than basal or squamous cell carcinoma of the skin;
 6). Patients with recent (<3 months) myocardial infarction, poorly controlled CHF, surgery for peripheral vascular disease, or coronary artery bypass surgery;
 7). Evidence of clinically significant or unstable active GI, hepatic or pulmonary disease;
 8). History of documented stroke or more than one confirmed TIA;
 9). Any condition which would make the patient or caregiver, in the opinion of the principal investigator unsuitable for the study; or
 10). Patients with known hypersensitivity to Donepezil HCL or other piperidine containing drugs.

EXAMPLE 2

Experimental Protocol

All subjects were provided a 5 week non-blinded treatment of donepezil, followed by a 48 week trial of hrIFN-a versus placebo superimposed on the continuing donepezil regimen in a randomized, double-blind, parallel group design. Although combined with donepezil, the double-blind treatment groups were labeled simply IFN and placebo for simplicity.

After a screening period of up to one month, the subjects were given donepezil 5 mg daily, and increased to 10 mg daily after two weeks. The subjects were maintained on the 10 mg daily dose of donepezil for an additional three weeks at which point they were seen for a baseline visit. At baseline, the subjects were randomized into the one of two active treatment (3,000 IU or 30,000 IU) IFN-a and placebo groups with repeat baseline MMSE, ADAS Cog ratings, as well as repeat baseline physical examination, EKG, CXR, and clinical lab determinations. Subjects received a continued supply of 10 mg donepezil and of the study medication (IFN-a or placebo) in forty-five day allotments.

The subjects were followed at six week intervals for a one year period. At each visit, clinical lab determinations, adverse event monitoring, vital signs, EKG, Cog ratings, ADFACS, MMSE were administered. At the exit visit, a physical exam was repeated (see Table 1). Follow-up blood studies to monitor for IFN-α toxicity were performed on all patients every six weeks.

The data were analyzed to evaluate and characterize changes during the 5-week open-label treatment with donepezil alone, but the primary analysis will focus on evaluation of the efficacy of IFN versus placebo in the 48 week double-blind trial.

The study medication was hrIFN-alpha interferon (Roferon). Patients in the active treatment arms receive dosages of either 3,000 or 30,000 international units hrIFN-a contained in 5 ml saline solutions ingested every day for 48 weeks+10 mg donepezil daily. The drug was discontinued when the subject experienced one of the following conditions: (1) persistently elevated liver function tests (3 times normal); (2) 5% weight loss; (3) persistently elevated temperature (38° C.); (4) decrease in white count (50% of baseline); or (5) absolute lymphocyte=2000. A complication form was submitted whenever a patient left the study prematurely, and also for any toxicity or deviation from protocol.

TABLE 1

FLOW SHEET

|  | Screen | donepezil 5 mg | donepezil 10 mg | baseline | six week visit | exit visit |
|---|---|---|---|---|---|---|
| informed consent | X | | | | | |
| psych/med hx | X | | | | | |
| PE | X | | | | | X |
| MMSE | X | | | X | X | X |
| CT scan | X | | | | | |
| EKG | X | | X | X | X | X |
| CBC, chem profile, UA | X | | | X | X | X |
| TFT, B12, folate, RPR | X | | | | | |
| ADAS-Cog | | | | X | X | X |
| Vitals | X | X | X | X | X | X |
| AE monitor | | X | X | X | X | X |
| CXR | X | | | | X | |

EXAMPLE 3

Primary Efficacy Measures

The Alzheimer's Disease Assessment Score, Cognitive Subscale (ADAS-Cog) is administered by a trained technician at baseline and at subsequent visits.

EXAMPLE 4

Secondary Efficacy Measures

Mini-Mental Status Examination (MMSE) is a brief test for quantifying the cognitive state of the patient. The 30 point test includes items evaluation orientation, recall, attention, language, and praxis. The MMSE is done by a trained technician at baseline and at subsequent visits.

The ratings for each domain are agreed upon by the members of the patient's assessment team, excluding the clinician performing the Cibic-plus, after review and consideration of the results from all the tests conducted during the clinic visit (ADAS-Cog, and MMSE).

EXAMPLE 5

Cell Preparation

Peripheral blood mononuclear cells (PMNC) were isolated from heparinized venous blood by means of a Ficoll-Hypaque density gradient (Pharmacia Fine Chemicals, Piscataway, N.J.), washed twice with Hanks balanced salt solution (GIBCO, Grand Island, N.Y.), counted, and resuspended in standard media consisting of 10% fetal calf serum (FCS) (Whittaker Bioproducts, Walkersville, Md.) in RPMI (Whitaker Bioproducts, Walkersville, Md.), with 2% glutamine (GIBCO), and 1% penicillin/streptomycin (GIBCO).

EXAMPLE 6

Measurement of Cytokine Secretion And Adhesion Molecules

Mononuclear cells (MNC) were unstimulated or stimulated with CD3, Con A, ionomycin/PMA. Supernatants were collected 2-7 days after activation and frozen at −70° C. after centrifugation. Interleukins were measured using solid phase ELISA commercial kit assays for IL-1, IL-6 (Biosource, Camarillo, Calif.) and TGF-β kits (Genzyme, Cambridge, Mass.). To determine the amount of sICAM-1 in serum samples diluted 1/10, commercial ELISA kits were used (Bender MedSystems, Vienna, Austria). To determine the amount of IL-1, IL-6, and $a_1$ACT in serum samples, commercial ELISA kits (above) or routine laboratory tests were performed.

EXAMPLE 7

Statistical Analysis

Following a five week non-blind donepezil adaptation period, during which the subjects were expected to evidence a modest cognitive improvement, a 48 week randomized, double-blind, parallel-groups design was used to evaluate the potential benefits from adding IFN-a to a continuing donepezil drug regimen.

Sample size calculations were based on an expected endpoint difference of 8 points on the ADAS cognitive subscale scores between the "IFN-a added" and "donepezil only" groups. This difference should correspond to an effect of $\Delta=1.0$ for the difference between IFN-a added and donepezil only groups at the end of 48 weeks of treatment. Based on these estimates, a two-sided a=0.05 ANOVA test require N=16 subjects per group for 80% power (or N=21/group for 90% power). A 90% power was chosen as insurance against errors in estimating magnitude of the treatment effect.

Two primary statistical methods were used for evaluating the therapeutic efficacy of IFN-a relative to donepezil only. The endpoint analysis was calculated on the simple difference between baseline and final measurement with baseline scores entered as a covariate. When drop-outs rates were different between the groups and exceed 20% across both groups, drop-out frequencies were entered either as numerical or categorical covariate for the endpoint analysis. The second type of analysis examined group differences and difference in group trends across the repeated measures. All of the repeated measurements were used in these analyses. Based on the data reported by others, it was anticipated that a reasonably homogeneous pattern of correlations among the repeated measures. If the correlational structure of the data appears to approximate compound symmetry, general linear model (GLM) tests were employed for the group main effect and linear trend difference using the Bonferroni correction for these two independent tests. These models require complete data, so last-observation-carried-forward (LOCF), was used to impute missing values for drop-outs. If the data evidence a clear autoregressive pattern of correlations, the general linear mixed model analysis was employed using SAS PROC-.MIXED with time treated as a regression variable across repeated measurements with an autoregressive AR(1) correlational structure. These analyses do not require imputing the missing values for drop-outs. All tests of significance were evaluated at a=0.05 with Bonferroni correction where differences in both average level and linear trends were considered as potential indicators of treatment effects.

EXAMPLE 8

Improved Cognitive Function In Patients With Alzheimer's Disease

Three subjects with Alzheimer's disease (AD), 3 in the placebo arm (on study drug 12 weeks) and 3 in the active treatment arm (2 with 30,000 IU and 1 with 3,000 IU) have enrolled. The subjects were provided a 5 week non-blinded treatment with Donepezil, followed by either hrIFN-alpha or placebo superimposed on the continuing Donepezil regimen in a randomized, double-blind, parallel group design for 48 weeks. Subjects were followed at six week intervals. At each visit, Alzheimer's Disease Assessment Score, Cognitive Subscale (ADAS-Cog) ratings and Mini-Mental Status Examination (MMSE) were administered. For MMSE scores, the higher the score, the better the memory with a maximum score=30. For ADAS scores, the higher the score, the worse the memory with a maximum score=70.

Table 2 shows the baseline and 48 week scores and the difference between entry and exit scores for the ADAS-Cog and Mini-Mental Status Examination. These data show that the 3 AD patients in the placebo group decreased in cognitive function increasing score) as measured by the ADAS-Cog, a sensitive and validated measure in Alzheimer's disease. The 3 active treatment group patient maintained or improved their cognitive function as assessed by the ADAS-Cog test.

TABLE 2

Improved Cognitive Function In Patients With Alzheimer's Disease

| Patient | MMSE Entry | MMSE exit | Δ |
|---|---|---|---|
| | placebo | | |
| 1 | 21 | 20 | −1 |
| 3 | 23 | 16 | −7 |
| 5 | 24 | 24 | 0 |
| | active | | |
| 2 | 9 | 8 | −1 |
| 4 | 13 | 10 | −3 |
| 6 | 22 | 19 | −3 |

| | ADAS-Cog entry | ADAS-Cog exit | Δ |
|---|---|---|---|
| | placebo | | |
| 1 | 22 | 29 | 7 |
| 3 | 14 | 33 | 19 |
| 5 | 17 | 22 | 5 |
| | active | | |
| 2 | 42 | 43 | 1 |
| 4 | 40 | 38 | −2 |
| 6 | 15 | 12 | −3 |

EXAMPLE 9

Marker For Ingested IFN-α Activity In Alzheimer's Disease

MxA is a type 1 IFN-specific induced mRNA/protein. It was recently demonstrated that mice splenocytes and human peripheral mononuclear cells demonstrated inducible levels of Mx mRNA signal after ingesting IFN-α. The relative levels of MxA mRNA signal were examined using quantitative PCR from peripheral mononuclear cells from Alzheimer's disease patients, comparing pre-ingestion to 4 hour post IFN-α ingestion. The relative numbers of transcripts for both human β-actin and human MxA were measured at pre-ingestion and 4 hours post-ingestion at each dose. The mean measured MxA transcript levels was normalized to the β-actin control (normalized mean=MxA mean/β-actin×100) and expressed as % β-actin molecules.

Human peripheral mononuclear cells from the 30,000 IU active treatment AD patient (n=2) demonstrated sustained levels of Mx mRNA (>3×baseline) after ingesting IFN-α for 48 weeks (Table 3). Human peripheral mononuclear cells from the 3,000 IU active treatment AD patient demonstrated unsustained levels of Mx mRNA after ingesting IFN-α for 48 weeks. This data suggest that the preservation of cognitive function in the active treatment patients is due to the ingested IFN-α because 30,000 IU>3,000 IU ingested IFN-α>>>placebo produces a previously described type I interferon biological response (MxA mRNA induction) without a similar response in the placebo patients.

TABLE 3

Induction of Marker For Ingested IFN-α Activity

| placebo #1 | Mx | placebo #3 | Mx | placebo #5 | Mx |
|---|---|---|---|---|---|
| Jan. 04, 2000 | 0.16 | Jan. 24, 2000 | 0.12 | Aug. 13, 2001 | 1.50 |
| Feb. 14, 2000 | 0.17 | Apr. 19, 2000 | 0.15 | Sept. 06, 2001 | 0.68 |
| May 08, 2000 | 0.11 | Jun. 01, 2000 | 0.16 | Oct. 18, 2001 | 1.57 |
| Jun. 26, 2000 | 0.12 | Jul. 13, 2000 | 0.15 | Feb. 12, 2002 | 1.56 |
| Aug. 02, 2000 | 0.10 | Aug. 25, 2000 | 0.12 | | |
| Oct. 26, 2000 | 0.29 | Oct. 05, 2000 | 0.29 | | |
| Dec. 07, 2000 | 0.16 | Nov. 14, 2000 | 0.22 | | |

| active #2 30K | Mx | active #4 30K | Mx | active #6 3K | Mx |
|---|---|---|---|---|---|
| May 31, 2001 | 0.78 | Apr. 06, 2000 | 0.08 | Mar. 29, 2002 | 0.41 |
| Jul. 31, 2001 | 3.28 | May 16, 2000 | 0.19 | Jun. 21, 2002 | 0.52 |
| Sept. 19, 2001 | 3.88 | Jun. 27, 2000 | 0.16 | Aug. 02, 2002 | 0.37 |
| Oct. 30, 2001 | 6.82 | Aug. 08, 2000 | 0.50 | Sept. 05, 2002 | 0.19 |
| Dec. 13, 2001 | 2.37 | Sept. 19, 2000 | 0.63 | Oct. 15, 2002 | 0.25 |
| Jan. 23, 2002 | 3.28 | Nov. 14, 2000 | 0.28 | Nov. 28, 2002 | 0.28 |
| Mar. 06, 2002 | 2.59 | May 30, 2002 | 0.76 | Jan. 04, 2003 | 0.39 |
| Apr. 18, 2002 | 2.61 | Jul. 19, 2002 | 1.09 | Mar. 01, 2003 | 0.42 |

The following references were cited herein:

Brod and Khan, Oral administration of murine IFN-α is more effective than parenteral administration in the suppression of relapses in EAE. J. Autoimmunity 9: 11-20 (1996).

Brod, Effect of oral administration of type 1 interferon on experimental autoimmune encephalomyelitis. Interferon Therapy in Multiple Sclerosis, ed., Reder, T., Marcel Dekker, pp 245-286 (1997).

Brod et al., Ingested IFN-α has biological effects in humans. Multiple Sclerosis Clinical and Laboratory Research 3:1-7 (1997).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed is:

1. A method of treating Alzheimer's disease in a patient comprising the step of administering to said patient effective amounts of an anti-cholinesterase agent and alpha interferon.

2. The method of claim 1, wherein said anti-cholinesterase agent is donepezil.

3. The method of claim 1, wherein said alpha interferon is administered from about 100 units per day to about 35,000 units per day.

4. The method of claim 1, wherein said alpha interferon is administered by a method selected from the group consisting of oral administration, subcutaneous injection, intravenous injection and intramuscular injection.

5. The method of claim 1, wherein said cognitive decline is caused by production or presence of cytokines.

* * * * *